United States Patent [19]

Cowper

[11] Patent Number: 5,315,863
[45] Date of Patent: May 31, 1994

[54] CONTINUOUS ON-LINE MEASUREMENT OF FLUID OR SLURRY RHEOLOGY

[75] Inventor: Norman T. Cowper, Northbridge, Australia

[73] Assignee: Slurry Systems Pty. Limited, New South Wales, Australia

[21] Appl. No.: 934,459

[22] PCT Filed: Aug. 18, 1991

[86] PCT No.: PCT/AU91/00096
§ 371 Date: Sep. 15, 1992
§ 102(e) Date: Sep. 15, 1992

[87] PCT Pub. No.: WO91/14167
PCT Pub. Date: Sep. 19, 1991

[30] Foreign Application Priority Data

Mar. 16, 1990 [AU] Australia ............................. 9165

[51] Int. Cl.⁵ .......................................... G01N 11/02
[52] U.S. Cl. .................................................. 73/54.09
[58] Field of Search ............... 73/54.01, 54.04, 54.09, 73/54.02, 54.07, 61.65, 61.67, 32 R, 438, 54.13

[56] References Cited

U.S. PATENT DOCUMENTS

| | | |
|---|---|---|
| 2,716,337 | 8/1955 | Heerlen ............................ 73/54.01 |
| 3,465,573 | 9/1969 | Shoemaker ....................... 73/54.01 |
| 3,520,179 | 7/1970 | Reed ................................. 73/54.04 |
| 3,554,010 | 4/1969 | van der Veen et al. ............ 73/438 |
| 3,839,901 | 10/1974 | Finkle et al. ...................... 73/54.01 |
| 3,839,914 | 10/1974 | Modisette et al. .................. 73/438 |
| 3,926,050 | 12/1975 | Turner et al. ...................... 73/438 |
| 4,024,753 | 5/1977 | Ouvrard ............................. 374/24 |
| 4,384,792 | 5/1983 | Sommers et al. .................. 374/36 |
| 4,680,957 | 7/1987 | Dodd ................................. 73/54.04 |
| 4,735,227 | 4/1988 | Royse et al. ....................... 73/54.01 |
| 4,890,482 | 1/1990 | Maini ................................ 73/54.14 |

Primary Examiner—Hezrone E. Williams
Assistant Examiner—Michael Brock
Attorney, Agent, or Firm—Banner, Birch, McKie & Beckett

[57] ABSTRACT

A rheometer or viscometer for continuously measuring the rheological properties of non-Newtonian, mixed phase fluids or slurries. The device has a vertically disposed, inverted U-tube to maintain solids in suspension and, therefore, exhibit a homogeneous character. The fluid flow rate is controlled to assure nonturbulent laminar flow through the tube. Pressure is measured at as point in each leg of the U-tube and compared. For a constant flow rate, the pressure drop over the tube is used to measure the viscosity of the fluid in the tube.

10 Claims, 1 Drawing Sheet

CONTINUOUS ON-LINE MEASUREMENT OF FLUID OR SLURRY RHEOLOGY

TECHNICAL FIELD

This invention relates to the continuous measurement of the rheological properties, such as viscosity and yield stress, of fliuds or slurries, especially fluids or slurries which exist in rugged industrial environments such as are found in the mining and mineral processing industries. More particularly the invention relates to the rheology measurements of fluids or slurries having significant quantities of entrained air or gases present and/or coarse (usually up to about 10 mm diameter) solid particles, varying ambient temperature and/or varying fluid or slurry temperature and pressure.

BACKGROUND ART

On-line viscometers are known for determining the yield stress and plastic viscosity of non-Newtonian or Bingham type fluids, calculated from formulae for laminar flow. However, in general, such known on-line viscometers are not capable of handling the extremes or demands which exist in the mining and mineral processing environments. For example, rotational types often suffer from reliability problems especially when applied to slurries. They also have difficulty in handling coarse solid particles and high process pressures. The static force measurement type viscometers are not suited to coarse particle slurries and will give erroneous readings when entrained air is present. Similar comments apply to vibrating element type viscometers.

The general technique of measuring the pressure differential between two points in a laminar fluid flowing through a tube of known diameter at a known rate is well known. This is shown, for example, in U.S. Pat. Nos. 3468158, 4680957 and 4384792. A technique using a vertical tube to measure slurry viscosity is shown in Australian Patent Application No. 31949/77. U.S. Pat. No. 3520179 discloses a rheometer or viscometer for non-Newtonian fluids using a capillary U-tube type apparatus, however this apparatus does not use differential pressure measurements, and further does not appear to be suitable for on-line measurements. U.S. Pat. No. 3465573 also discloses a U-tube type arrangement, but uses a comparison between two different paths, rather than the mere U-tube, to produce a measurement.

U.S. Pat. No. 4680957 (Dodd) would appear to be the most relevant reference to the present invention in that it discloses a viscosity level conduit to measure viscosity. However one of the main problems with this type of viscometer is the tendency for solids to settle out of solution along the conduit thus adversely affecting the accuracy of readings from the viscometer. There is no suggestion of the use of a U-tube in this specification.

DISCLOSURE OF INVENTION

It is an object of the present invention to overcome the above and other disadvantages by the provision of a method and apparatus for the measure of a fluid or slurry rheology or viscosity.

This object may be achieved, in accordance with the present invention, by the provision of a rheometer comprising an inlet for a sample of a non-Newtonian fluid to be measured, a vertically disposed inverted U-tube conduit connected to said inlet at one end and to an outlet at its other end, pressure differential measurement means operatively mounted across the said U-tube and flow meter and control valve means disposed between said outlet and said other end of the U-tube.

The present invention further provides a method for measuring and monitoring the rheological properties of a fluid or slurry flowing through a vertically disposed inverted U-tube conduit, comprising the steps of (a) providing a stream of fluid or slurry through said U-tube conduit in non-turbulent laminar flow;

(b) determining the pressure differential across the U-tube; and (c) further determining the rheology or viscosity therefrom.

The invention provides a basis for on-line adjustment of slurry consistency and rheology by more efficient usage of chemical reagents and modifiers, resulting in substantial modifiers, resulting in substantial cost reductions.

BRIEF DESCRIPTION OF THE DRAWINGS

In order that the reader may gain a better understanding of the present invention, hereinafter will be described a preferred embodiment thereof, by way of example only and with reference to the accompanying drawing (FIG. 1) which is a schematic representation of an on-line rheometer or viscometer in accordance with the present invention.

BEST MODE FOR CARRYING OUT THE INVENTION

Figure 1:
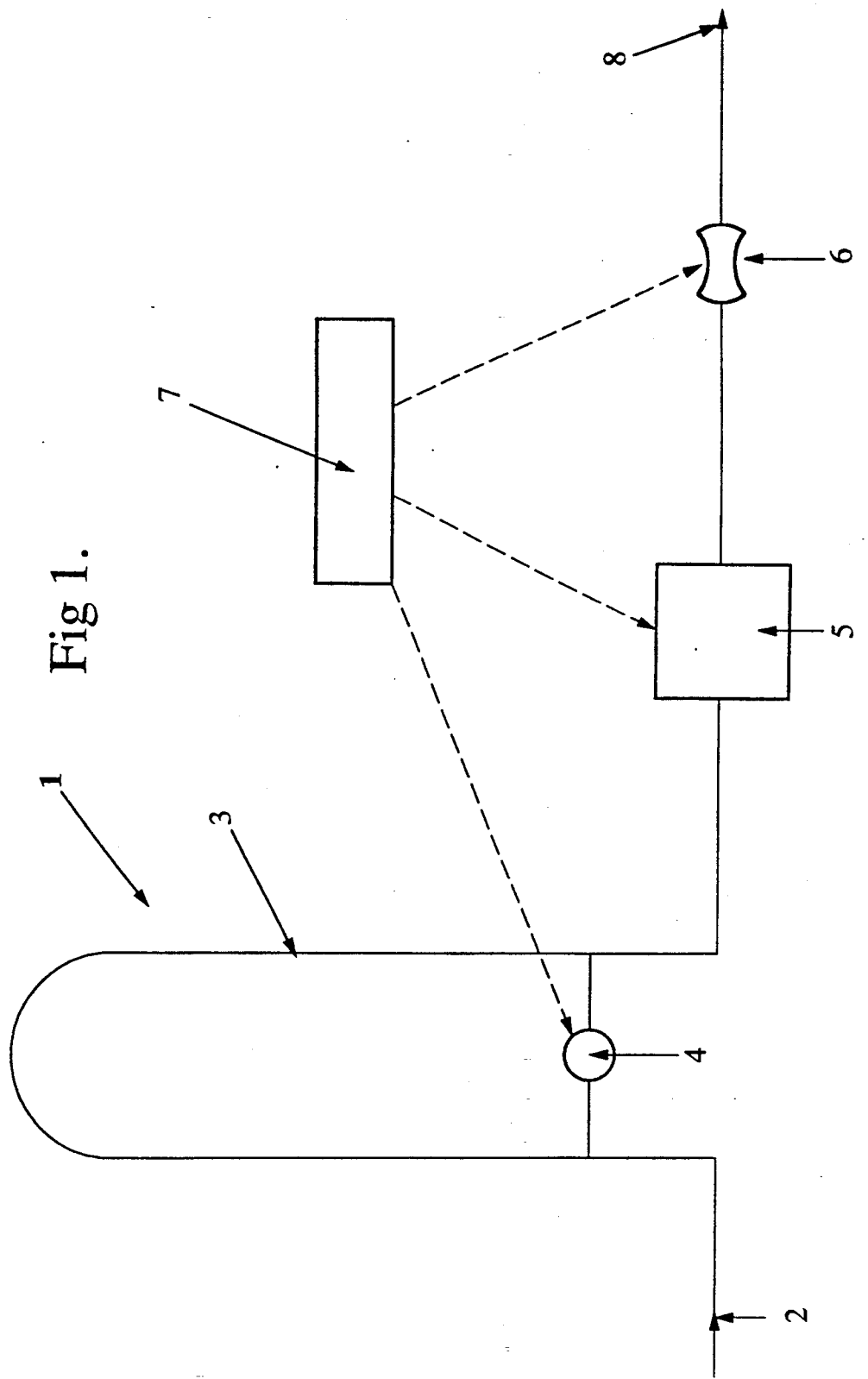

Referring to FIG. 1 the rheometer or viscometer 1 comprises an inlet conduit 2 being a sub-stream from, and in parallel with, the main slurry transport conduit (not shown) leading into a vertically disposed inverted U-tube section of the conduit 3 through which the slurry or fluid is caused to flow either by gravity or by pumping. The differential pressure across the U-tube is measured by means of a transducer or transmitter 4 mounted directly onto the U-tube. The flow rate is controlled by means of a magnetic flow meter 5 and a control valve 6 under the operative control of a microprocessor 7. The slurry or fluid then passes back via outlet conduit 8 to the main slurry transport conduit (not shown).

The chosen flow rate and the internal diameter of the U-tube 3 are such that laminar rather than turbulent flow prevails in the U-tube. For a constant flow rate the differential pressure across the U-tube 3 is then a measure of the fluid or slurry rheology or viscosity. The U-tube is inverted and disposed in a vertical plane to ensure that the fluid or slurry passing therethrough is thoroughly mixed or homogenous. In horizontal flow a laminar stream has little capacity to maintain coarse particles in suspension. As a result the particles tend to settle in a horizontally disposed conduit thus increasing the pressure gradient. A vertically flowing stream, on the other hand, has a far greater capacity to maintain coarse solids in suspension, and it is for this reason that the U-tube 3 is disposed vertically.

It is common practice to isolate pressure transmitters from the process fluid or slurry by means of an oil-filled diaphragm and capillary arrangement. However, these exhibit some sensitivity to ambient temperature which is especially significant at the low differential pressures measured in the apparatus according to the present invention. To overcome this the pressure transmitter 4 is mounted directly between the two legs of the U-tube 3 with the process fluid or slurry being in direct contact with the diaphragms of the pressure transmitter. Errors due to ambient temperature changes are thereby eliminated.

The flow rate is measured by the magnetic flow meter 5 the diameter of which is less than the U-tube 3 so as to generally result in turbulent flow within the flow meter. This ensures the fluid or slurry is as homogeneous as possible to improve the accuracy of flow measurement.

The flow rate signal is directed to the computer 7 which controls the control valve 6. This valve is of the hydraulically actuated constricting muscle type with a concentric round hole construction. Such valves are ideal for slurries and will pass coarse particles and give a long life. With the 25 mm size valve normally used in the present case particles up to 10 mm are easily handled.

In industrial plants significant quantities of entrained air or gases are often present in the process fluid or slurry. As noted previously this can result in erroneous readings in some presently available instruments. In the present device air or gas can accumulate in the downstream leg of the U-tube 3 thereby introducing an additional static pressure component resulting in errors in measurement. To overcome this the computer 7 is programmed to periodically open the control valve 6 fully to provide a high flow rate flushing action. The flow rate during this flushing period is sufficiently high so as to ensure turbulent flow within the U-tube. This turbulence, together with the high velocity of flow, ensures the removal of all air or gas together with any coarse solids which may have accumulated in parts of the conduit. During the flush cycle the viscometer output signal is "frozen" at the value just prior to the start of the flush cycle.

The frequency and period of the flush can be programmed to suit the particular plant conditions. The computer processes and averages the signal from the differential pressure transmitter and displays the result in the selected rheology units. In the case of mineral slurries their rheological behaviour is often described by the Bingham Plastic model. For such slurries the differential pressure measured across the U-tube is nearly proportional to the Bingham Yield Stress so the output can be displayed in Yield Stress units if desired.

All components used in the present invention, such as the differential pressure transmitter, the magnetic flow meter and the control valve are well proven in the harsh environment of mineral processing plants. Maximum reliability is therefore ensured. All of these components are capable of operation at high process pressures and temperatures. There are no moving parts in contact with the process fluid or slurry other than the slight flexing of the control valve sleeve. This ensures reliability and maximum wear resistance.

In summary it is the unique combination of vertical U-tube, direct mounted pressure transmitter, periodic flushing action and the use of proven components which results in an on-line viscometer capable of meeting all the extreme demands required of an on-line viscometer.

INDUSTRIAL APPLICABILITY

The on-line viscometer according to the present invention is applicable to the on-line measurement and modification or adjustment of viscosity of all fluids or slurries including those having entrained air or gases present and those having coarse (typically up to 10 mm) solid particles present. The invention provides a basis for on-line adjustment or modification of slurry consistency and rheology by more efficient usage of chemical reagents and modifiers normally used in such situations, resulting in substantial cost reductions for the process as a whole. The viscometer is not affected by ambient or process temperature changes and is capable of measuring viscosity at high process pressures and temperatures. In this regard and in its tolerence to corrosive fluids it is limited only by the capability of the component parts which are available in types to suit most applications.

I claim:

1. The combination of an apparatus for on-line measurement of fluid rheology and a fluid flowing therein, said combination comprising:
   a non-Newtonian fluid containing entrained air and/or coarse solids, and
   an apparatus comprising:
   (a) a substantially vertically disposed, inverted U-shaped tube forming an upflowing inlet arm and a downflowing outlet arm,
   (b) means for maintaining a constant rate of nonturbulent laminar flow through said tube, and
   (c) means for measuring the pressure differential between a point in said inlet arm and a point in said outlet arm of said tube.

2. The combination according to claim 1, wherein said means for maintaining comprises a flowmeter, a control valve, and means for opening or closing said control valve in response to the measurement signal from said flowmeter.

3. The combination according to claim 2, wherein said flowmeter is a magnetic flowmeter.

4. The combination of claim 3 wherein said magnetic flow meter exhibits a diameter that is sufficiently less than the diameter of said U-shaped tube to result in turbulent flow through said flow meter.

5. The combination according to claim 1, wherein said fluid is a slurry or a liquid having gas entrained therein.

6. The combination according to claim 5, further comprising means for purging the apparatus to remove accumulated gases and solid particles.

7. The combination of claim 1 wherein said means for measuring comprises a pressure transmitter mounted between said inlet arm and said outlet arm and providing direct contact between fluid in each arm and diaphragms in said pressure transmitter.

8. Apparatus for on-line measurement of fluid rheology, said apparatus comprising in combination:
   a substantially vertically disposed, inverted U-shaped tube;
   means for maintaining a constant rate of flow through said tube wherein said means comprises a flowmeter, a control valve, and means for opening or closing said control valve in response to a measurement signal from said flowmeter; and
   means for measuring the pressure differential between a point in each of the two arms of said tube.

9. Apparatus according to claim 8 further comprising:
   means for purging said apparatus to remove accumulated gases and solid particles.

10. Apparatus for on-line measurement of fluid rheology, said apparatus comprising in combination:
    a substantially vertically disposed, inverted U-shaped tube;

means for maintaining a constant rate of flow through said tube;

means for measuring the pressure differential between a point in each of the two arms of said tube; and means for purging said apparatus to remove accumulated gases and solid particles.

* * * * *